United States Patent [19]

Nieberlein

[11] 4,116,634

[45] Sep. 26, 1978

[54] VOID, FLAW, AND CRACK INDICATOR FOR EPOXY BONDS

[75] Inventor: Vernon A. Nieberlein, Huntsville, Ala.

[73] Assignee: The United States of America as represented by the Secretary of the Army, Washington, D.C.

[21] Appl. No.: 836,327

[22] Filed: Sep. 26, 1977

[51] Int. Cl.² ............................................. G01N 21/16
[52] U.S. Cl. .................................. 23/230 R; 73/104; 427/8; 23/230 L
[58] Field of Search ......................... 23/230 R, 230 L; 116/114 AM; 73/104; 427/386, 8; 8/4

[56] References Cited

U.S. PATENT DOCUMENTS

| | | | |
|---|---|---|---|
| 2,079,925 | 5/1937 | Reichert | 23/230 R |
| 2,884,339 | 4/1959 | Dannenberg | 427/386 X |
| 3,490,873 | 1/1970 | Corl | 23/230 R |
| 3,652,224 | 3/1972 | Johnson et al. | 23/230 R |
| 3,652,225 | 3/1972 | Coffin, Jr. et al. | 23/230 R |

FOREIGN PATENT DOCUMENTS 826,121  12/1959  United Kingdom ..................... 73/104

*Primary Examiner*—Morris O. Wolk
*Assistant Examiner*—Arnold Turk
*Attorney, Agent, or Firm*—Nathan Edelberg; Robert P. Gibson; Jack W. Voigt

[57] ABSTRACT

A method for locating imperfections including voids, bubbles, cracks, and flaws in cured epoxy resin articles. These imperfections which are too small to be readily seen with the naked eye, or that are normally very inconspicuous become visible when an indicator solution is applied to the epoxy resin imperfection. The indicator solution is selected from a 0.1 percent alcoholic solution of bromcresol purple, bromthymol blue, thymol blue, meta-cresol purple, xylenol blue, aurin, methyl violet, lacmoid, and resazurin for locating imperfections in epoxy resins cured with an alkaline curing agent such as an amine. The indicator solution is selected from a 0.1 percent alcoholic solution of congo red, p-sulfo-o-methoxybenzene, and azodi-methyl-alpha-naphthylamine for locating imperfections in epoxy resins cured with an acidic curing agent.

3 Claims, No Drawings

VOID, FLAW, AND CRACK INDICATOR FOR EPOXY BONDS

DEDICATORY CLAUSE

The invention described herein may be manufactured, used, and licensed by or for the Government for governmental purposes without the payment to me of any royalties thereon.

BACKGROUND OF THE INVENTION

Epoxy resins have found wide use in the hybrid microelectronic industry, in aerospace applications, and elsewhere as a bonding agent between various types of ceramic, plastic, metal, wood, and composite components. In many of these applications it is imperative that the epoxy bond be free of imperfections such as voids, cracks and other flaws. However, these imperfections are often so small or otherwise so inconspicuous that they escape detection since they are not readily seen with a naked eye.

Desirable would be a method which would assist in the detection of imperfections in cured epoxy resin articles. Particularly desirable would be a method which is simple to employ and which would make these inconspicuous imperfections readily visible.

Therefore, an object of this invention is to provide a method for locating imperfections in cured epoxy resin articles by making them readily visible.

A further object of this invention is to provide a method for locating imperfections in cured epoxy resin articles which are cured with an alkaline curing agent such as an amine.

Another object of this invention is to provide a method for locating imperfections in cured epoxy resin articles which are cured with an acidic curing agent.

SUMMARY OF THE INVENTION

The method of this invention employs an indicator solution selected from a 0.1 percent alcoholic solution of bromcresol purple, bromthymol blue, thymol blue, meta-cresol purple, xylenol blue, aurin, methyl violet, lacmoid, and resazurin for locating imperfections in epoxy resin articles cured with an alkaline curing agent such as an amine. The indicator solution is selected from a 0.1 percent alcoholic solution of congo red, p-sulfo-o-methoxybenzene, and azodi-methyl-alpha-naphthylamine for locating imperfections in epoxy resin articles cured with an acidic curing agent.

A drop of the selected indicator solution is added to the surface of a cured epoxy resin article to be tested for imperfections. The indicator solution readily penetrates extremely small openings and dyes the surface of such openings a color which is characteristic of the selected indicator solution for the alkaline or acidic condition present. The basis for the selection of the indicator solution and the cured epoxy resin article for testing relates to the fact that the curing agent, either alkaline or acidic, causes the cured epoxy resin to exhibit either an alkaline or acidic characteristic in the presence of a pH indicator solution. The result is a fine dark line where the indicator penetrates a small crack, thus rendering a previously inconspicuous crack visible to the naked eye.

DESCRIPTION OF THE PREFERRED EMBODIMENTS

The method of this invention employs an indicator solution selected form a 0.1 percent alcoholic solution of bromcresol purple, bromthymol blue, thymol blue, meta-cresol purple, xylenol blue, aurin, methyl violet, lacmoid, and resazurin for locating imperfections in epoxy resin articles cured with an alkaline curing agent such as an amine. When an acidic curing agent (e.g. carboxy-terminated polymeric curing agents) is used for curing the epoxy resin the indicator solution is selected from a 0.1 percent alcoholic solution of congo red, p-sulfo-o-methoxybenzene, and azodi-methyl-alpha-naphthylamine.

The method of this invention provides a means for locating voids, bubbles, cracks, and flaws in cured epoxy resin articles that are too small to be readily seen with the naked eye, or that are normally very inconspicuous.

The representative procedure of this invention includes providing a cured epoxy resin article to be tested for imperfections, adding a drop of the selected indicator solution (0.1 percent bromcresol purple and 0.1 percent bromthymol blue) to the area of the epoxy resin to be tested for imperfection; and observing the change in appearance of epoxy resin. The indicator solution readily penetrates extremely small openings and dyes the surface of such openings a deep blue which is easily detected.

Evaluating the effectiveness of method of this invention was completed by testing three strips of epoxy resins cured with an amine. The stripes of cured epoxy were bonded to gold plated Kovar. After adding a drop of the selected indicator solution to the center of the epoxy resin stripes cured with an amine exhibiting the alkaline characteristics the dyes penetrated the center of each epoxy stripe to render a row of extremely small bubbles, that formed during curing and that were not readily visible to the naked eye, readily visible as a fine dark line down the center of the epoxy stripe. Photographs in color of the test specimen very distinctly showed the imperfection that was made visible by the dye that penetrated to dye the surface of the imperfection. The true nature of the imperfection can be evaluated further by inspection under magnification and/or by photographic evaluation.

The effectiveness of the method of this invention was also evaluated by adding a drop of indicator solution to the bond line between a transparent epoxy and aluminum. The solution penetrated the bond line in many places showing the extent of defective bond.

Since most epoxies are amber colored, those indicators which turn yellow or orange at the prevailing surface pH do not appear suitable. The best choice for visibility are those indicators which turn purple or blue, with green as a third choice.

Table I, below, lists indicators which are preferred for testing epoxy resins cured with acidic curing agents. Mixtures of the indicators can also be used effectively.

TABLE I

| Indicator | Color Change |
| --- | --- |
| Congo red | blue, below pH 3.5 |
| p-Sulfo-o-methoxybenzene | blue, below pH 3.5 |
| Azodi-methyl-alpha-naphthylamine | blue, below pH 3.5 |

Table II, below, lists indicators which are preferred for testing epoxy resins cured with amine curing agents which exhibit alkaline characteristics. Mixtures of the indicators can also be used effectively.

TABLE II

| Indicator | Color Change |
|---|---|
| Thymol blue | blue, above pH 9 |
| Meta-cresol purple | purple, above pH 8.5 |
| Xylenol blue | violet, above pH 8 |
| Aurin | purple, above pH 7 |
| Methyl violet | violet, above pH 6 |
| Lacmoid | blue, above pH 6 |
| Resazurin | violet, above pH 6 |

Although the experiments and testings of the indicators of Tables I and II employed a 0.1 percent alcoholic solution for the method of this invention, other solvents for the indicators at other concentrations should be effective for use in locating imperfections in cured epoxy resin articles.

I claim:

1. A method for testing for and locating imperfections including voids, bubbles, cracks, and flaws having an opening to a surface of cured epoxy resin of a cured epoxy resin article comprising completing the steps of:
   (i) providing a cured epoxy resin article to be tested, said cured epoxy resin selected from the group consisting of an epoxy resin that is cured with an amine curing agent which results in alkaline characteristics in said amine cured epoxy resin and a cured epoxy resin that is cured with a carboxy-terminated polymeric curing agent which results in acidic characteristics in said carboxy-terminated polymeric cured epoxy resin;
   (ii) adding to the surface of said cured epoxy resin article an indicator solution selected from the group consisting of a 0.1 percent alcoholic solution of bromcresol purple, bromthymol blue, thymol blue, meta-cresol purple, xylenol blue, aurin, methyl violet, lacmoid, resazurin, and mixtures thereof when testing for and locating imperfections in epoxy resins cured with said amine curing agent or adding to the surface of said cured epoxy resin article an indicator solution selected from the group consisting of a 0.1 percent alcoholic solution of congo red, p-sulfo-o-methoxybenzene, azodimethyl-alpha-naphthylamine, and mixtures thereof when testing for and locating imperfections in epoxy resins cured with said carboxy-terminated polymeric curing agent;
   (iii) examining said cured epoxy resin article to which said selected indicator solution has been added for evidence of penetration by said indicator a site of imperfection wherein the surface of said imperfection is dyed a color that is characteristic of said indicator solution for the alkaline or acid characteristic of said cured epoxy resin at the site of imperfection, said dyed surface of an imperfection rendering a previously inconspicuous imperfection visible which serves to locate and identify the imperfection in said cured epoxy resin article.

2. The method of claim 1 wherein said indicator solution selected for testing an amine cured epoxy resin article is a mixture of bromcresol purple and bromthymol blue.

3. The method of claim 1 wherein said examining includes inspection under magnification to evaluate the nature of a located imperfection.

* * * * *